United States Patent [19]

Komakine

[11] Patent Number: 4,608,256

[45] Date of Patent: Aug. 26, 1986

[54] METHOD OF TREATING CACHEXIA

[76] Inventor: Chukei Komakine, 13-10, Azasugidaira, Taira, Iwaki-shi, Fukushima-ken, Japan

[21] Appl. No.: 717,590

[22] Filed: Mar. 29, 1985

Related U.S. Application Data

[63] Continuation-in-part of Ser. No. 503,692, Jun. 13, 1983, abandoned.

[30] Foreign Application Priority Data

Oct. 1, 1982 [JP] Japan ................................ 57-170923

[51] Int. Cl.⁴ .............................................. A61K 33/26
[52] U.S. Cl. ................................................... 424/147
[58] Field of Search ........................................ 424/147

[56] References Cited

U.S. PATENT DOCUMENTS 3,836,676  9/1974  Komakine .............................. 426/74

FOREIGN PATENT DOCUMENTS 150858  11/1980  Japan .
1381238  1/1975  United Kingdom .

*Primary Examiner*—Donald B. Moyer
*Assistant Examiner*—John W. Rollins, Jr.
*Attorney, Agent, or Firm*—Frishauf, Holtz, Goodman & Woodward

[57] ABSTRACT

An inorganic health preservative for treating cachexia to improve the physical constitution of humans which is prepared by mixing 8 parts by weight of crystalline ferrous sulfate heptahydrate, which is a by-product of manufacturing titanium-white, with 1 to 2 parts by weight of fine powder of flyash, which is a by-product in a steam power station, drying the mixture for about one hour at a temperature of from 65° to 85° C. to obtain shattered granules, and pulverizing mechanically said shattered granules into a finely powered substance, having the degree of pulverization of about 100 Tyler mesh.

2 Claims, No Drawings

METHOD OF TREATING CACHEXIA

This application is a continuation-in-part of application Ser. No. 503,692 filed June 13, 1983 now abandoned.

BACKGROUND OF THE INVENTION

This invention relates to an inorganic health preservative whose regular daily use in small amounts improves the physical constitution of humans afflicted with cachexia.

As set forth in the Japanese published Unexamined Patent Application Ser. No. 150858/1980, the present inventor discovered that a material manufactured by a method similar but not the same as that of the present invention was very effective as an antiseptic additive to general compound feed for domestic animals, poultry and cultured fish. Namely, it was found that general compound feeds mixed with 0.5 to 1.0% by weight of the above-mentioned material had the advantages that the rotting and fermentation of the aforementioned feeds during storage was eliminated; the animals which took a feed mixed with said material were completely free of various diseases; excrement from these animals was rendered substantially odorless; the farms could maintain a clean environment, suppressing the offensive odors which hitherto unavoidably permeated the surroundings of the farms; and the meat of the animals which took the aforesaid feed mixed with said medical material was improved in taste. Futhermore, the fat of the meat was reduced; and the death rate of the animals and their offsprings were noticeably decreased. Thus, livestock and poultry breeders and fishermen enjoyed great success with the above-mentioned material.

Hitherto, expensive organic synthetic sterilizers or antibiotics were applied as antiseptic additives to general compound feeds and also as medical materials for sick animals. In recent years, however, it has been noted that such synthetic sterilizers or antibiotics lead to the growth of cancer in humans who eat the meat or eggs of animals raised by feeds mixed with said antiseptic or antibiotic additives. Accordingly, the Ministry of Health and Welfare of Japan finally prohibited the addition of any of the above-mentioned organic medical materials to animal feeds. At present, however, no effective substitute has been found for these organic medical materials. Consequently, feed dealers, fish culturists and animal raisers have been quite at a loss what to do. Moreover, the supervising government administration has failed to find a proper method of guiding the dealers of the aforesaid antiseptic or antibiotic materials.

In such circumstances as mentioned above, the present inventor disclosed an invention of a purely inorganic feed additive in the aforesaid Japanese Patent Application as a result of studies and experiments conducted over ten years. This invented inorganic feed additive has been officially approved by the Japanese government to be able to eliminate the aforesaid difficulties and to realize the noticeable effects. In 1982, the director of the Science and Technology Administration of the Japanese government granted a letter of commendation of the present inventor.

A product embodying the above-mentioned invention is a greyish white powderly inorganic antiseptic which is to be added to general compound feeds. This product is manufactured by mixing 1 to 2 parts by weight of flyash with 8 parts by weight of crystalline ferrous sulfate heptahydrate ($FeSO_4.7H_2O$), and drying the mixture at a temperature of 65° to 85° C. for about 30 minutes while stirring to obtain shattered granules of the almost neutralized mixed product.

Crystalline ferrous sulfate heptahydrate is a substantially useless, strongly acidic and deliquescent coarse granular substance having a pH value of about 3, which can be obtained as a by-product in the manufacture of titanium white using sulfuric acid. To date, manufactures of titanium-white have been extremely troubled with the disposal of this by-product. Hitherto, the by-product has been transported to the open sea and dumped therein.

When thermally dried for about 30 minutes at a temperature of 64° to 85° C., the coarse granular crystals of ferrous sulfate heptahydrate break by themselves into shattered granules. At this time, part of the water of crystallization is evaporated, causing the heptahydrous crystals to turn into a stable white or faintly green shattered substance mainly consisting of ferrous sulfate monohydrate. Ferrous sulfate has long been utilized as a blood-making medicine.

Flyash is formed of very fine globular particles obtained when the vapor of coal ash melted at a temperature of about 1,200° C. is cooled in a flue during the burning of coal in a steam power station. The flyash is generally recovered by a dust collector. The flyash is a grayish white powdery by-product which consists of inorganic oxides activated by high temperature and has high alkalinity with the pH value estimated at about 12. The flyash contains extremely small amounts of oxides of P, Ca, Mg, K, Na, B, Mo, Mn, Se, Pb and Cu as the so-called minerals. Although part of the by-product flyash is sometimes applied as a lubricant to be mixed with cement mortar, the greater part of it is wasted.

When the coarse crystals of ferrous sulfate heptahydrated mixed with the aforementioned percentage of flyash are thermally dried at a temperature of 65° to 85° C. for about 30 minutes, the crystals naturally break into shattered granules, causing part of the water of crystallization to be removed. Further, the surfaces of the shattered granules are covered with the fine powder of flyash, cohering to the granules. As a result, hygroscopicity of the ferrous sulfate is prevented, thereby improving the slipperiness of the shattered granules. The particles of ferrous sulfate and those of flyash are mutually neutralized, causing the pH value of the mixed mass to be reduced to a low alkalinity of about 9. When this low alkaline substance is added to animal feeds, the feeds as a whole indicate also very low alkalinity, and is rendered suitable for the preservation of the health of animals together with the effect of minerals contained in the feed.

Addition of 0.5 to 1.0% by weight of this additive to a general compound feed has an advantage that the mixed feed can be safely stored for five months during summer season, whereas general compound feeds destitute of said additive rot within a month's storage in the summer time. The further merits of said additive are that animals which have eaten the compound feeds mixed with this additive have improved blood circulation, and are free from various diseases; almost all domestic animals, which have hitherto tended to become sick, can dispense with medicine; the death rate of infant pigs becomes almost zero percent; their excrement does not decompose but has a substantially oderless semisolid form, whereby the environment in which the animals are raised being prominently improved; the minerals contained in the additive enable harmful substaces grown in the animal body to be excreted out therefrom; and a synergistic effect of ferous sulfate and flyash enable the animals to have good health free from almost all diseases.

SUMMARY OF THE INVENTION

The present inventor has conceived that, if a human were to take the inorganic feed additive set forth in the published unexamined patent application Ser. No. 150858/1980 as a human health preservative, then the same merit would be obtained as in the case of animals.

The present inventor asked many sickly weak people to take said inorganic feed additive on a trial basis. For many years, to a large number of poultry and domestic animals were given the aforesaid inorganic animal feed additive with their feed to ascertain the practical effect. The public agricultrual experiment stations in the various districts proved the advantageous effects of the inorganic feed additive. Further, the director of the Science and Technology Agency of the Japanese Government has awarded the present inventor a prize as mentioned afore in recognition of the prominent merit of this inorganic additive. Therefore, the present inventor entertains no anxiety about the direct application of this inorganic additive to humans.

Those who took the inorganic additive as a health preservative for a few or several months praised unanimously its prominent effects. Moreover, no case has hitherto been cited wherein this health preservative had a harmful side effect during a long habitual use time of period.

When using the inorganic animal feed additive set forth in the aforesaid Japanese patent application as a health preservative for humans, it has some shortcomings that said agent is felt to be unpleasant at the taking time and is somewhat unstable because of its some coarse particle formation. Therefore, the method of manufacturing said additive has been slightly modified in the present invention.

Namely, the crystals of by-product ferrous sulfate heptahydrate mixed with the prescribed percentage of flysh are heated at a temperature of 65° to 85° C. for about one hour. Thus, the water of crystallization contained in the ferrous sulfate heptahydrate crystals is removed to a slightly larger extent than applied afore in order to increase the stability of the crystals. Further, the dried mixture is finally pulverized mechanically to about 100 Tyler mesh or less to assure the homogenization and stabilization of the product.

DETAILED DESCRIPTION OF THE PREFERRED EMBODIMENT

When an adult takes 0.5 to 1.0 gram of the above-mentioned low alkaline health preservative agent twice a day, once immediately after breakfast and once after supper, he will be in a cheerful mood in several days and will notice that his physical strength is increases.

When the subject agent is orally applied intact, the tongue and teeth are blackened by the effect of the ferrous component thereof, yet with no harming result. Therefore, it is necessary to take the agent included in a medical wafer or enclosed in a capsule. Further, the excrement of a person who has taken this health preservative turns jet-black with no harming effect. Since, however, the appearance of this black color results from the complete excretion of injurious substances retained in the human body, it is unnecessary to feel any anxiety about this event. The cessation of application of the preservative eliminates immediately the black color from the excrement.

When a man, who feels that his constitution is abnormal, namely, a person surffereing from cachexia, takes the subject health preservative, his unusual constitution will be restored to its original healthy state, namely, the cachexia will be alleviated. Thus, the present invention provides a method for treating humans afflicted with cachexia by administering to said humans the subject health preservative. Ailments other than virus diseases result from the unusual condition of the constitution of human body. For instance, when a man feels fatigue, shoulder stiffness or lumbago, the intake of the subject health preservative for several days releases effectively him from such ailments, completely eliminating the necessity of resorting to acupuncture. Since the subject health preservative does not contain any harmful organic chemical compound, the long continuous application of this health preservative does not cause any undesirable side effect at all.

Furthermore, the health preservative of this invention is characterized in that it can be commerically manufactured by a simple process at a very low cost from useless industrial by-products which have been proved hygienically safe.

Sometimes the application of the subject health preservative for about two weeks temporarily causes the user to suffer from a slightly abnormal constitution, for instance, diarrhoea, as in the case with common Chinese medicines or with known health preservative prepared from chlorophyta, for example, chlorella. However, this phenomena is a positive proof that the subject health preservative is effective. Therefore, the user should take the health preservative continuously without any fear.

The effects of the health preservative of this invention will become more apparent with reference to the examples which follow.

EXAMPLES

EXAMPLE 1

A 74 year old man had been annoyed by insomnia for about 20 years. His physician administered continuously a psychosomatic stabilizer to the patient. Three years ago, he began to feel to pain in the articulations of knees and foot-thumbs, and finally could not walk without a walking stick.

In the meanwhile, he chanced to be informed of the subject health preservative, and he took one gram of said preservative after breakfast every day. In two months, he could enjoy good sleep and found it unnecessary to take any psychosomatic stabilizer, and moreover was released from pain in the joints and could walk without walking stick.

EXAMPLE 2

A 65 year old man, suffereing from pollakisuria for several years, was finally forced to wake up hourly at night to urinate. Three months after the intake of the subject health preservative, he only had to urinate every four or five hours.

EXAMPLE 3

A 70 year old man, who had suffered from auricular fibrillation for 15 years, always had a pulse of over 85 pulsations per minute, and was hospitalized for 50 days, but without success. After leaving the hospital, he began to take the subject health preservative.

Moreover, the old man sometimes had a fit of cardiac asthma and received medical examination and medication twice a month from a physician. Four months after the intake of the subject preservative, no cardiac asthma took place. Before the intake of the health preservative, his blood pressure was 170 to 180 systolic and 100 to 110 dystolic. However, three months after the intake of the health preservative, his blood pressure was restored to a normal level, i.e. 140 to 150 over 80 to 90.

EXAMPLE 4

A 49 year old manager of a bank brach office greatly suffered from physical stress due to his extremely busy work. Three weeks after the intake of the subject health preservative, however, he felt no fatigue and recovered his sexual appetite which has previously been at an ebb.

EXAMPLE 5

A 25 year old man underwent two surgical operations for empyema, but without success. He continued to be bothered as much as before by the constant ejection of green stinking nasal mucus. He suffered from a stuffy nose and headache and felt a decline in his vitality. Three months after the intake of the subject health preservative, however, he enjoyed a pleasent feeling.

EXAMPLE 6

The subject health preservative was administered to six languid hospitalized pregnent women. About two weeks after administration, they recovered their vigor and effected successful deliveries at full term. Three boys and three girls thus born grew into such robust babies as could hardly be expected from the previously hospitalized sick women. The babies had better pulse pressure and greater body-weight than the standard.

EXAMPLE 7

A 51 year old woman, who suffered from neuralgia after leaving the hospital where she was operated for cancer of the breast, underwent acupuncture, but without success. Three months after the intake of the subject health preservative, she recovered her physical strength, becoming more portly than before.

EXAMPLE 8

A 75 year old man, who had continued all day long the work of reading small letter literatures such as patent publications and preparing manuscripts for more than 20 years, grew noticably senile from about two years ago and had weakened eyesight. In the evening he became purblind, failing to clearly decipher small letters.

Two months after the intake of the subject health preservative, he felt no fatigue even when reading or writing all day long.

EXAMPLE 9

A 62 year old man, who had been afflicted since birth with perspiring palms which remained wet even during the winter time, suffered always from a complex that his defective palms might cause a person shaking hands with him to leave an unpleasant feeing. Two months after the intake of the subject health preservative, the perspiration of his palms was completely eliminated, enabling him to calmly shake hands with others.

EXAMPLE 10

A 64 year old man, who had been afflicted with indisposition due to the occurrence of nauseous languidness and occasional fever, was diagnosed by a physician. As a result, it was found that he was suffering from chronic hepatitis, with the GOT and GPT values respectively determined to be 150 and the overall cholesterol value to be 360. The physician told him that no suitable medical treatment was currently available for chronic hepatitis, and he should advisably refrain from overwork in order to supress the further development of said chronic hepatitis. The patient began to take in the subject health preservative upon recomendation of his acquaintance. The physician's examination four months after the intake of said health preservative indicated that the GOT value fell to 35, the GPT value to 40 and the overall cholesterol value to 185, proving that the patient had recovered from chronic hepatities. For reference, healthy persons have generally GOT value of 80 to 40, GPT value of 5 to 35 and overall cholesterol value of 130 to 250.

EXAMPLE 11

An 39 year old man, who had been seriously injured in a motor accident, underwent blood transfusion during the surgical operation. Unfortunalely, the blood transfusion led to the occurrence of acute serum hepatities after three years. The serum hepatitis, which appeared to be cured at one time, relapsed into chronic serum hepatitis two years later, with the ZTT value determined to be 18. Then, months after the intake of the subject health preservative, however, the GOP value fell to 22, the GPT value to 36 and the ZTT value to 7. For reference, a healthy man has usually a ZTT value lower than 12.

EXAMPLE 12

A 59 year old man who had been afflicted with allergic nettle rash about 20 years never failed to suffer from nettle rash when he ate shrimp, crab, egg, milk, sardine, mackerel, octopus or mackerel-pike. Therefore, he ceased to eat any of these foods. Later, he happened to be informed of the meritorious effect of the subject health preservative. He took it for trial for sometime. About 40 days later, he was forced to eat chicken and egg with rice. The next morning no nettle rash appeared. Encouraged by this event, he continued to take the subject health preservative.

EXAMPLE 13

A 36 year old woman, who had suffered from anemia for long time, indicated a systolic blood pressure of 70 to 80 and dystolic blood pressure of 50 to 60, feeling usually dizzy and unstable walking. The intake of the subject health preservative for more than three months improved her blood pressure to the standard level, that is, about 120 over 80. She could sleep soundly at night, was saved from constipation, and had restored vigor.

What is claimed is:

1. A method for treating humans afflicted with cachexia comprising orally administering to a human afflicted with cachexia an amount of an inorganic composition effective to treat said cachexia, said inorganic composition being prepared by mixing 8 parts by weight of crystalline ferrous sulfate heptahydrate with 1 to 2 parts by weight of flyash; heating the mixture for about one hour at a temperature of 65° to 85° C. to thereby cause granules of said mixture to shatter and to form an almost neutralized mixture; and mechanically pulverizing said shattered granules into a finely powdered inorganic composition.

2. The method of claim 1, wherein the degree of pulverization of said finely powdered inorganic composition is about 100 Tyler mesh.

* * * * *